United States Patent
Dubois

(10) Patent No.: US 10,317,656 B2
(45) Date of Patent: Jun. 11, 2019

(54) OPTICAL COHERENCE TOMOGRAPHY APPARATUS AND METHOD USING LINE CONFOCAL FILTERING

(71) Applicants: CENTRE NATIONAL DE LA RECHERCHE SCIENTIFIQUE, Paris (FR); INSTITUT D'OPTIQUE GRADUATE SCHOOL, Palaiseau (FR); UNIVERSITE PARIS SUD 11, Orsay (FR)

(72) Inventor: Arnaud Dubois, Orsay (FR)

(73) Assignees: CENTRE NATIONAL DE LA RECHERCHE SCIENTIFIQUE, Paris (FR); Institut d'Optique Graduate School, Palaiseau (FR); UNIVERSITE PARIS SUD 11, Orsay (FR)

( * ) Notice: Subject to any disclaimer, the term of this patent is extended or adjusted under 35 U.S.C. 154(b) by 157 days.

(21) Appl. No.: 15/106,164

(22) PCT Filed: Dec. 19, 2014

(86) PCT No.: PCT/EP2014/078867
§ 371 (c)(1),
(2) Date: Jun. 17, 2016

(87) PCT Pub. No.: WO2015/092019
PCT Pub. Date: Jun. 25, 2015

(65) Prior Publication Data
US 2016/0320598 A1   Nov. 3, 2016

(30) Foreign Application Priority Data
Dec. 20, 2013   (FR) ..................... 13 63234

(51) Int. Cl.
*G02B 21/00* (2006.01)
*G01B 9/02* (2006.01)
(Continued)

(52) U.S. Cl.
CPC .......... *G02B 21/0064* (2013.01); *A61B 90/37* (2016.02); *G01B 9/02091* (2013.01);
(Continued)

(58) Field of Classification Search
CPC ........ G01B 9/02091; A61B 2090/3735; A61B 90/37; G06T 2207/10072; G06T 7/0012;
(Continued)

(56) References Cited

U.S. PATENT DOCUMENTS 6,480,285 B1 * 11/2002 Hill .................... G01B 9/04
356/492
7,884,947 B2 * 2/2011 De Lega ............ G01B 9/02044
356/511
(Continued)

FOREIGN PATENT DOCUMENTS

EP    1 364 181 A1   11/2003
EP    1 586 931 A2   10/2005
(Continued)

OTHER PUBLICATIONS

S. Kim et al., "Simultaneous measurement of refractive index and thickness by combining low-coherence interferometry and confocal optics," Optics Express, vol. 16, No. 8, Apr. 14, 2008, pp. 5516, XP055137008.
(Continued)

*Primary Examiner* — Michael P LaPage
(74) *Attorney, Agent, or Firm* — Osha Liang LLP

(57) ABSTRACT

An optical tomography apparatus comprises: a polychromatic light source, a one-dimensional optical sensor, an interferometric microscope, a one-dimensional confocal spatial filtering system, an actuation system making it possible to perform a one-way scan depthwise of an object to be observed and a processor for reconstructing a two-dimensional image of a section of the object from a plurality of
(Continued)

one-dimensional interferential images acquired by the image sensor during the one-way scan. An optical tomography method based on use of such an apparatus is also provided.

16 Claims, 4 Drawing Sheets

(51) Int. Cl.
*A61B 90/00* (2016.01)
*G02B 21/33* (2006.01)
*G02B 21/36* (2006.01)
*G06T 7/00* (2017.01)

(52) U.S. Cl.
CPC ....... *G02B 21/008* (2013.01); *G02B 21/0032* (2013.01); *G02B 21/0056* (2013.01); *G02B 21/33* (2013.01); *G02B 21/367* (2013.01); *G06T 7/0012* (2013.01); *A61B 2090/3735* (2016.02); *G02B 21/0036* (2013.01); *G06T 2207/10072* (2013.01); *G06T 2207/30004* (2013.01)

(58) Field of Classification Search
CPC ...... G06T 2207/30004; G02B 21/0056; G02B 21/0064; G02B 21/367; G02B 21/008; G02B 21/33; G02B 21/0032; G02B 21/0036
See application file for complete search history.

(56) References Cited

U.S. PATENT DOCUMENTS

| | | | |
|---|---|---|---|
| 2002/0021491 A1 | 2/2002 | Engelhardt | |
| 2009/0046298 A1* | 2/2009 | Betzig | G01N 21/6445 356/521 |
| 2010/0141954 A1* | 6/2010 | Kobayashi | G01B 9/02007 356/479 |
| 2011/0043661 A1* | 2/2011 | Podoleanu | A61B 3/102 348/239 |
| 2011/0235045 A1* | 9/2011 | Koerner | G02B 21/0056 356/451 |
| 2011/0261367 A1* | 10/2011 | Gmitro | A61B 5/0066 356/479 |
| 2012/0307258 A1* | 12/2012 | Koerner | G01B 9/0209 356/497 |
| 2013/0182096 A1* | 7/2013 | Boccara | A61B 5/0066 348/79 |
| 2013/0314717 A1* | 11/2013 | Yi | G02B 21/0032 356/479 |
| 2014/0028974 A1* | 1/2014 | Tumlinson | A61B 3/102 351/206 |
| 2015/0077760 A1* | 3/2015 | Koerner | G01B 9/02008 356/496 |

FOREIGN PATENT DOCUMENTS

| | | |
|---|---|---|
| EP | 2 447 754 A1 | 5/2012 |
| FR | 2 962 531 A1 | 1/2012 |
| JP | 2009-020448 A | 1/2009 |
| JP | 2009-505051 | 2/2009 |
| WO | 2007/017589 A1 | 2/2007 |

OTHER PUBLICATIONS

Y. Chen et al., "High-Resolution Line-Scanning Optical Coherence Microscopy," Optics Letters, vol. 32, No. 14, Jul. 15, 2007, pp. 1971-1973, XP001506730.

Van Velthoven et al., "Recent developments in optical coherence tomography for imaging the retina," Progress in Retinal and Eye Research, vol. 26, No. 1, Dec. 14, 2006, pp. 57-77, XP005803711.

A. Dubois et al., "Thermal-light full-field optical coherence tomography in the 1.2um wavelength region," Optics Communications, vol. 266, No. 2, Oct. 15, 2006, pp. 738-743, XP028080898.

Arnaud Dubois et al., "Ultrahigh-resolution full-field optical coherence tomography," Applied Optics, vol. 43, No. 14, May 10, 2004, pp. 2874-2883.

A.F. Fercher et al., "Optical coherence tomography-principles and applications," Institute of Physics Publishing, Reports on Progress in Physics, vol. 66, 2003, pp. 239-303.

Office Action issued in corresponding Japanese Patent Application No. 2016-541612, dated Nov. 6, 2018 (6 pages).

* cited by examiner

OPTICAL COHERENCE TOMOGRAPHY APPARATUS AND METHOD USING LINE CONFOCAL FILTERING

CROSS-REFERENCE TO RELATED APPLICATIONS

This application is a National Stage of International patent application PCT/EP2014/078867, filed on Dec. 19, 2014, which claims priority to foreign French patent application No. FR 1363234, filed on Dec. 20, 2013, the disclosures of which are incorporated by reference in their entirety.

FIELD OF THE INVENTION

The invention relates to an optical tomography apparatus and method, intended in particular, but not exclusively, for biological and medical, and notably histological, applications. Other possible applications relate for example to the characterization of materials.

BACKGROUND

The histological study of tissues taken by biopsy are of great use in clinical practice, for example for diagnosing tumors. However, this technique is slow and complex to implement, because it requires a biopsy, that is to say the taking of a sample of the tissue to be studied, and for it to be cut into thin slices which are observed by microscope and analyzed by an anatomical pathologist. The full procedure also requires the fixing of the sample, the occlusion thereof in a matrix and the coloring thereof. That poses a problem, above all in the case of examinations made during surgical operations, where speed is of primordial importance. Furthermore, the sampling step can be annoying, even dangerous, for the patient (in the case of the brain for example). For this reason, non-intrusive—notably optical—imaging techniques have been developed to view the internal structure of the biological tissues—or more generally of semi-transparent objects. To be able to compete with the conventional histological examinations, these techniques have to make it possible to access in situ to a depth of the order of a millimeter below the surface of the tissue and exhibit a resolution of the order of a micrometer. The speed of execution, the simplicity and the cost are also important parameters to be taken into account.

None of the imaging techniques known from the prior art gives full satisfaction.

Scanning optical coherence tomography (OCT) is a technique based on "white" (wide band) light interferometry. In its version in the time domain, a beam of white light is divided into two parts, one focused on the tissue to be studied and the other on a reference mirror. The light reflected (backscattered) by the observed object is combined with that reflected by the reference mirror and detected by a photodetector. An interference occurs only when the optical path difference is at most of the order of the coherence length of the radiation; by modifying the optical length of the reference arm of the interferometer, different depths are accessed in the object. An image in 2 or even 3 dimensions can be constructed using interferometry (which allows acquisition according to the axial dimension, that is to say the depth) and scanning (which allows acquisition according to one or two lateral dimensions). In scanning OCT in the frequency domain, the reference arm has a fixed optical length and the interferometric signal is spectrally analyzed. In this respect, see the article by A. F. Fercher "*Optical coherence tomography—principles and applications*", Reports on Progress in Physics 66 (2003) 239-303. In practice, only with difficulty does OCT make it possible to obtain lateral resolutions better than approximately a few micrometers.

A more recent technique, full field OCT, uses a two-dimensional image sensor to detect the interferometric signals. This technique, coupled with the use of a light source of low temporal and spatial coherence such as a halogen lamp, makes it possible to substantially improve the spatial resolution—both laterally and depthwise (axially) compared to scanning OCT. However, this technique is ill-suited to applications in which the object is likely to move (particularly for in vivo applications), then leading to scrambling of the interferometric signals. Moreover, it provides "face wise" sections (parallel to the surface of the observed object), whereas vertical sections are often more useful. Furthermore, its depth of penetration is less than in scanning OCT. This technique is described, for example, in the document EP1364181 and in the article by A. Dubois, K. Grieve, G. Moneron, R. Lecaque, L. Vabre, and A. C. Boccara "Ultrahigh-resolution full-field optical coherence tomography", Applied Optics 43, p. 2874 (2004).

The article by S. Kim et al. "Simultaneous measurement of refractive index and thickness by combining low-coherence interferometry and confocal optics", Optics Express, Vol. 16, No. 8, 5516 (14 Apr. 2008) describes a method which combines confocal optics and interferometry with low coherence length to characterize a sample by determining its thickness and its refractive index. It is not an imaging method, much less tomographic.

Confocal microscopy uses a spatial filtering to select the light originating from a small region of the observed object; a two- or three-dimensional image can then be reconstructed by scanning. The document EP 2 447 754 describes a slit chromatic confocal microscopy device and method. This system requires:
  an illumination in polarized light
  an objective having strong chromatic aberrations; and
  a spectrometer for measuring the spectrum of the light at the output of the microscope, this measurement making it possible to access the depth probed in the object.

In this device, the role of the slits is to generate spectral lines (their width defining the spectral resolution and therefore the spatial resolution depthwise in the object). They do not have a confocal filtering role.

The document EP 1 586 931 describes another slit confocal microscopy device and method, which simplifies the process of image reconstruction by allowing for the simultaneous acquisition of a number of pixels along a line. The confocal microscopy, used without fluorescent markers, offers a depth of penetration substantially less than in scanning OCT and in full-field OCT.

The article by Yu Chen et al. "*High-resolution line-scanning optical coherence microscopy*", Optics Letters Vol. 32, No. 14, 15 Jul. 2007, pages 1971-1973 describes an apparatus and a method combining slit confocal microscopy and scanning OCT that makes it possible to obtain "face wise" sections of a sample with a higher sensitivity than in full-field OCT. The axial resolution achieved is approximately 3 μm and the lateral resolution approximately 2 μm, these results being obtained by using a very costly femtosecond pulsed laser as light source.

The nonlinear microscopy techniques (two-photon, harmonic generation and other such forms of microscopy) exhibit performance levels—in terms of depth of penetration, spatial resolution and acquisition rate—comparable to those of full-field OCT but at the price of a higher cost and generally longer acquisition times.

The cost and complexity of implementation are also among the main drawbacks of the non-optical imaging techniques, such as X microtomography (which also exhibits a low acquisition rate) and magnetic resonance imaging MRI (the spatial resolution of which is mediocre compared to the optical methods).

SUMMARY OF THE INVENTION

The invention aims to overcome at least some of the abovementioned drawbacks of the prior art. More particularly, it aims to provide a technique for viewing the internal structure of semi-transparent objects such as biological tissues that makes it possible to obtain vertical sections (orthogonal to the surface of the object) at a high rate (several sections per second), with a high spatial resolution (of the order of 1 µm, both axially and laterally) and a satisfactory depth of penetration (of the order of a millimeter). The invention also aims to provide a technique suited to in vivo and in situ applications.

One subject of the invention that makes it possible to achieve this aim is an optical tomography apparatus comprising: a polychromatic light source; a one-dimensional optical sensor; an interferometric microscope comprising: a first arm, called reference arm, at the end of which is arranged a so-called reference mirror; a second arm, called object arm; a beam splitter coupling said first and second arms to said polychromatic light source and to said sensor; and at least one objective, said reference mirror being arranged to correspond with a focusing plane of said objective or of one said objective placed in the reference arm; a one-dimensional confocal spatial filtering system, cooperating with said polychromatic light source to illuminate an object to be observed, arranged at the end of said object arm, along a line, called observation line, lying in said focusing plane of said objective or of one said objective placed in the object arm, said one-dimensional confocal spatial filtering system being also arranged to select the light backscattered by said object and originating from said observation line, and to form a one-dimensional image of said line on said sensor; characterized in that it also comprises: an actuation system configured to displace said observation line parallel to an optical axis of said objective or of one said objective placed in the object arm so as to perform a one-way scan of said object, while maintaining a zero optical path difference between, on the one hand, a first trajectory going from said beam splitter to said reference mirror and back by traveling along said reference arm and, on the other hand, a second trajectory going from said beam splitter to said observation line and back by traveling along said object arm; and a processor programmed or configured to reconstruct a two-dimensional image of a section of said object to be observed, oriented parallel to said optical axis of said objective or of one said objective placed in the object arm, from a plurality of one-dimensional interferometric images acquired by said sensor corresponding to different positions of said observation line during said one-way scan.

According to different embodiments of such an apparatus:
Said actuation system can be configured to provoke a relative displacement, parallel to said optical axis of said objective, or of one said objective placed in the object arm, of said object to be observed relative to said interferometric microscope, without modifying the optical lengths of said reference arm and of said object arm.

Said actuation system can be configured to displace the objective in the focusing plane of which said observation line is located and to modify the optical length of said reference arm so as to maintain the zero optical path difference between said first trajectory and said second trajectory.

The apparatus can also comprise a dispersion compensation device arranged on at least one out of said object arm and said reference arm, said actuation system being configured to act also on said dispersion compensation device during said one-way scan.

Said interferometric microscope can be a Linnik microscope, comprising a first objective arranged on said reference arm and a second objective arranged on said object arm, said reference and object arms being separate. As a variant, it can be chosen from a Michelson microscope and a Mirau microscope, comprising a single objective.

Another subject of the invention is an optical tomography method comprising the following steps:
a) providing a polychromatic light source;
b) using a beam splitter to direct a first fraction of light emitted by said source along a first trajectory, called reference trajectory, and a second fraction of light emitted by said source along a second trajectory, called object trajectory;
c) using an objective cooperating with a one-dimensional confocal spatial filtering system to focus said second fraction of light so as to illuminate a semi-transparent object to be observed along a line, called observation line, situated in a focusing plane of said objective, and to collect the light backscattered by said duly illuminated object;
d) using said objective, or another objective, to focus said first fraction of light on a reference mirror arranged on said reference trajectory, and to collect the light reflected by said mirror;
e) using said beam splitter to combine the light backscattered by said object with the light reflected by said mirror and direct it to a one-dimensional optical sensor;
f) using said one-dimensional confocal spatial filtering system to select the light originating from said observation line, and to form therefrom a one-dimensional image on said sensor;
g) using an actuation system to displace said observation line parallel to an optical axis of said objective so as to perform a one-way scan of an object to be observed on said object trajectory, while maintaining a zero optical path difference between said reference trajectory and said object trajectory; and
h) using a processor to reconstruct a two-dimensional image of a section of said object to be observed, oriented parallel to said optical axis, from a plurality of one-dimensional interferometric images acquired by said sensor corresponding to different positions of said observation line during said one-way scan.

According to different embodiments of such a method:
Said step g) can be implemented by provoking a relative displacement, parallel to said optical axis, of said object to be observed relative to said interferometric microscope without modifying the optical lengths of said reference arm and of said object arm.
Alternatively, said step g) can be implemented by displacing the objective in a focal plane of which said observation line is located and by modifying the optical length of said reference arm so as to maintain the zero optical path difference between said first trajectory and said second trajectory.

The method can also comprise a step i) of compensation of the modifications of the dispersion induced by the displacement of the observation line inside said object to be observed during said one-way scan.

BRIEF DESCRIPTION OF THE DRAWINGS

Other features, details and advantages of the invention will emerge on reading the description given with reference to the attached drawings given by way of example and which represent, respectively.

DETAILED DESCRIPTION

Figures 1A, 1B:
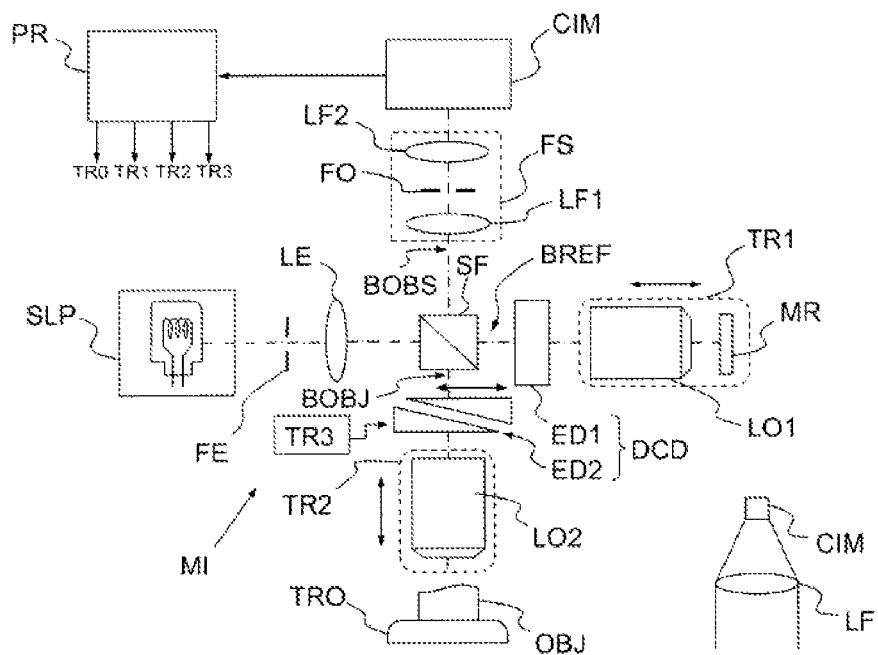
FIG. 1A, a schematic diagram of an optical tomography apparatus according to an embodiment of the invention, based on a Linnik interferometric microscope.
FIG. 1B, a detail of an optical tomography apparatus according to a variant of said embodiment of the invention.

FIG. 1A illustrates an optical tomography apparatus according to an embodiment of the invention. This apparatus essentially consists of a "Linnik" interferometric microscope modified by the addition of spatial filtering means (FE, FS), a system (DCD) for compensating dispersion differences between the two arms of the interferometer, a one-dimensional optical sensor (CIM) and a processor programmed or configured appropriately (PR).

This apparatus comprises a polychromatic light source SLP. The latter is schematically represented by an incandescent light bulb, but it could preferably be a source of higher luminance, such as a light-emitting diode or an association of light-emitting diodes, a superluminescent diode or an association of superluminescent diodes, a halogen filament lamp, an arc lamp even a laser or laser-based source (a source by "supercontinuum" generation for example). In all cases, its spectral width (at mid-height) will preferably be greater than or equal to 100 nm; the greater this spectral width, the better will be the axial resolution of the apparatus; the band center wavelength can be visible or be located in the near infrared; in the biological and medical applications, preference is generally given to the near infrared, typically between 600 nm and 1500 nm. The source can be polarized or non-polarized, spatially coherent or incoherent. The spatially coherent sources (of laser or superluminescent diode types) may be advantageous because of their greater luminance, but they can introduce coherence "noise": spurious interference phenomena leading to a reduction of the relative amplitude of the useful interferometric signal and a lack of uniformity of lighting. Furthermore, the use of spatially coherent sources substantially increases the overall cost of the apparatus.

A slit FE and a lens LE form an illuminating optical system cooperating with the source SLP and the interferometric microscope to illuminate an object OBJ to be observed along a line. If the polychromatic light source is spatially coherent, the slit FE can be replaced by a beam-forming optic, incorporating, for example, a convergent or divergent cylindrical lens, in order to illuminate the object along a line having a width of the order of a micrometer (more specifically, the width of the line is of the order of magnitude of the lateral resolution of the imaging system).

The illuminating beam formed by the lens LE is directed to a beam splitter, in this case, a splitter cube—SF. The latter directs a first portion of the incident beam along a first arm of the interferometric microscope, called "reference arm", BREF, and a second portion of the incident beam along a second arm BOBJ, called "object arm". A first microscope objective LO1 and a so-called "reference" mirror MR are arranged on the reference arm; the objective focuses the light on the mirror, then collects the light reflected thereby and directs it—in the reverse direction—along the reference arm, or trajectory. A second microscope objective LO2, of focal length identical to that of said first objective LO1, is arranged on the object arm; the objective focuses the light on the object OBJ to be observed, then collects the light backscattered thereby and directs it—in the reverse direction—along the object arm, or trajectory. Typically, the objectives have a numerical aperture of between 0.1 and 1.0 (contrary to traditional scanning OCT, there is here no field depth constraint which would limit the numerical aperture to be employed). It is interesting to note that these objectives can be in air or immersed; by contrast, in the case of full-field OCT, immersion objectives are used, which can be restrictive in certain applications.

The beam splitter SF recombines the light beams originating from the two objectives, allowing them to interfere, and redirects them along a so-called "observation" arm BOBS.

The contrast of the interference fringes is maximum when the two beams which interfere exhibit a same intensity; consequently, it may be advantageous to use a weakly reflecting reference mirror or to provide an attenuator on the reference trajectory.

A one-dimensional spatial filter FS is arranged on the observation arm. In the embodiment of FIG. 1A, it is a confocal filter, comprising two lenses LF1, LF2. A slit FO is placed in the rear focal plane of the lens LF1. The lens LF2 forms an image of the slit FO on the one-dimensional optical sensor CIM. The slit FO is optically conjugate with the slit FE associated with the source SLP; in other words, the interferometric microscope forms an image of the slit FE on the slit FO and vice-versa. As will be explained later, with reference to FIGS. 3A and 3B, that is a "confocal" configuration; in effect, the source SLP, the slit FE, the lens LE, the splitter SF, the objective LO2, the spatial filter SF form a slit confocal microscope.

The one-dimensional optical sensor CIM (linear camera), consisting of a single row of pixels (square or rectangular), or a few (typically not more than 10 or 20, and at most 100) rows of pixels, detects the light at the output of the filter. It is also possible to use a single row of pixels, or the combination of a few (more often than not up to 10 or 20) rows of pixels, adjacent or close, of a matrix image sensor.

As a variant (illustrated in FIG. 1B), the spatial filtering can be performed without the filtering system FS, by positioning the one-dimensional optical sensor CIM in the focal plane of a single lens LF.

Furthermore, if a slit FO is present on the side of the detector (or the detector itself serves as slit as explained previously, FIG. 1B), it is possible to omit the illumination slit FE (or the beam-forming system replacing it), at the cost of a potentially lower detection sensitivity.

The apparatus also comprises an actuation system consisting of a plurality of translation stages—TR1, TR2, TR3 and TRO—and a processor PR driving them. Not all these translation stages necessarily need to be present at the same time; in particular, if TRO is present, TR1 and TR2 can be omitted, and, conversely, if TR1 and TR2 are present, TRO can be omitted.

The reference mirror MR and objective LO1 assembly is displaced axially by means of a first translation stage TR1 of said actuation system; consequently, the objective LO2 must also be displaced, by means of a respective translation stage TR2, also forming part of said actuation system. When the objective LO2 is lowered (that is to say is translated toward the object) by a distance "e", the reference mirror MR and the objective LO1 are displaced by $$\left(n_{im} - 1 - \frac{n_{object}^2}{n_{im}}\right)e,$$

$n_{im}$ being the refractive index of the immersion medium of the objectives—gel, liquid or air ($n_{im}$=1)—and $n_{object}$ being the refractive index of the object.

As a variant, it would be possible to vary the axial distance between just the object OBJ and the interferometric microscope, by leaving the different elements of the interferometric microscope stationary. For that, it is possible to displace all the interferometric microscope (displacement system not represented) or the object OBJ by means of the translation stage TRO; this can be considered in particular with immersion objectives.

In all cases, that has the effect of modifying the depth to which the object OBJ is probed: an observation line LDO, situated in the focal plane (more generally, in the focusing plane) of the objective LO2, produces a scan of said object "depth wise", that is to say in the direction of the optical axis of said objective. The actuation system must at the same time displace this observation line and ensure that the optical path difference between the reference trajectory and the object trajectory (up to the observation line, which is considered to constitute the end of the object arm) remains zero or at most less than the coherence length of the polychromatic light source and the depth of field of the objective. This scan modifies the thickness of the object passed through by the light propagating along the object arm BOBJ, and therefore the dispersion that it undergoes. A device DCD is provided to compensate this modification of the dispersion. The device DCD comprises an element with constant dispersion ED1—for example a block of glass, material which has a dispersion close to that of the object OBJ—arranged in one of the arms of the interferometer and an element with variable dispersion ED2 arranged in the other arm of the interferometer. The element ED2 consists of two prisms arranged facing one another; by displacing one of the prisms relative to the other, the thickness of glass passed through, and therefore the optical trajectory in this arm, is modified. It is also possible to use a glass plate inclined relative to the optical trajectory; the thickness of glass passed through is modified by acting on the angle of inclination. Other systems can be considered; the general idea is that it is necessary to vary the optical thickness in one of the arms in order to equalize the dispersion in the two arms of the interferometer (or at least reduce the difference) whatever the imaging depth.

In other embodiments, the dispersion compensation device can consist more simply of an immersion medium (typically a drop of liquid with a refractive index that is close to that of the object) of which the thickness in the object arm reduces as the objective approaches the object to be observed (see FIGS. 5A to 5F). The reduction of the thickness of the immersion medium is compensated by the increase in the thickness passed through in the object: thus, the dispersion in the object arm remains constant, equal to that in the reference arm.

In the embodiment of FIG. 1, the device DCD is actuated by a third translation stage TR3, also forming part of said actuation system. That makes it possible to produce a dynamic compensation of the dispersion, synchronized with the other displacements.

As a variant, it is possible to use a variable thickness of transparent dispersive material, such as glass, placed in one of the arms of the interferometer to modify both the optical path and the dispersion. This variable thickness can be produced, for example, using a double prism, like the device DCD of FIG. 1, or a simple orientable plate. In this case, it may not be necessary to displace the objective LO1 and mirror MR assembly.

The detector CIM acquires line images corresponding to a plurality of different positions of the line imaged in the object. This stack of line images can be processed digitally to obtain an image of a vertical section of the object.

A simple approach consists in using the so-called phase-shift interferometry method, consisting in digitally combining a number of phase-shifted line images. For example, it is possible to combine four line images corresponding to positions of the observation line spaced apart by $\lambda/8$ in the axial direction, $\lambda$ being the central wavelength of the illuminating light in the object. That corresponds to a phase shift of $\pi/2$ between two adjacent images. If $E_1$, $E_2$, $E_3$, $E_4$ are used to denote these images, $(E_1-E_3)^2+(E_2-E_4)^2$ corresponds to the amplitude of the interference signal—that is to say to the amplitude of the reconstituted image—and $(E_1-E_3)/(E_2-E_4)$ corresponds to the phase of the interference signal. This phase can provide information other than structural and tomographic information on the object. It is essential to note that there is no contradiction between the concept of phase offset, or phase shift, and the fact, mentioned above, that the observation line always corresponds to an optical path difference between the object and reference arms that is equal to zero. In effect, any structure of the object, likely to backscatter the light, is not observed only when it coincides with the observation line, but also before and after (because the coherence "gate" and that introduced by the confocal filtering have a width greater than $\lambda$). There is therefore indeed a phase offset between the contributions of this structure to the images acquired in succession during the axial scan.

As a variant, the stack of line images can be processed by Fourier analysis in order to extract the envelope of the interference fringes (the amplitude of the interference signal) and eliminate the non-modulated part of the signal (non-interferometric signal).

It should be stressed here that, in accordance with the invention, the one-way scan of the object over all the depth imaged in order to produce an image in axial cross section also makes it possible to acquire, at the same time, an interferometric signal (obviously, a second one-way scan can then be performed in the opposite direction). However, both in the abovementioned technique of Yu Chen et al. and in full-field OCT, there is no scan of the depth of the object to acquire the interferometric signal. The latter is acquired using a variable and periodic phase shift produced by displacement of the reference mirror over a total range typically less than 1 micrometer.

A three-dimensional image of the object can be obtained by juxtaposing adjacent section images. That requires a scan in a direction at right angles both to the acquisition line and to the optical axis of the objective LO2. This scan can be obtained by displacing the object (or, in an equivalent manner, the interferometric microscope, or the illumination line) by means of a lateral translation stage.

A same processor PR can drive the actuators TR1, TR2, TR3 and, if necessary, TR0 (which may not be, or may not be solely, translation stages) and process the stacks of line images acquired by the sensor CIM, these tasks being interdependent. The processor PR can be a dedicated device, comprising one or more microprocessors, or a computer equipped with appropriate interface cards. As a variant, two distinct processors can be used to drive the actuation system and to reconstruct the images.

Figures 2A, 2B:
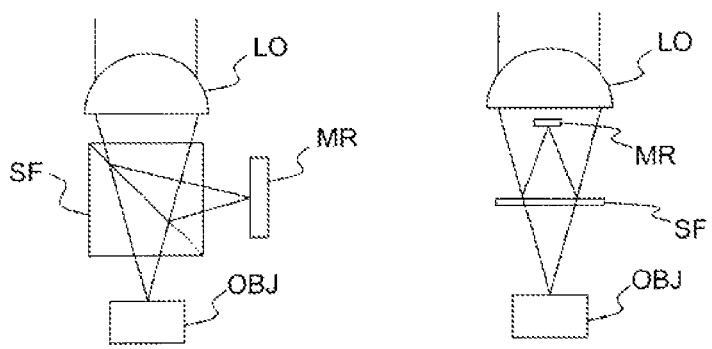
FIGS. 2A, 2B, other possible embodiments of the invention based on the configurations of Michelson and Mirau interferometric microscopes.
Figure 5A:
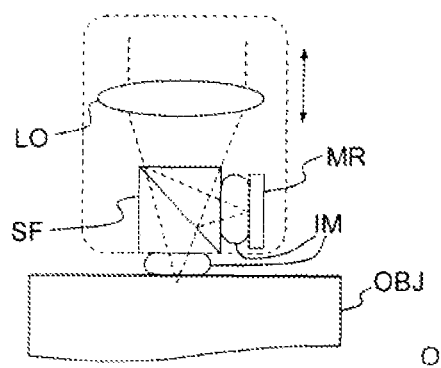
FIGS. 5A to 5G, different embodiments of the invention based on Michelson and Mirau interferometric microscopes and using an immersion medium.
Figure 5B:
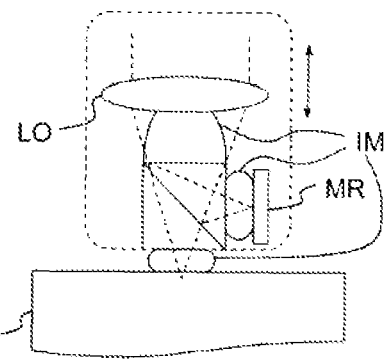

The invention has been described with reference to a particular embodiment, based on a Linnik interferometric microscope. However, other types of interferometric microscopes exist and are suitable for implementing the invention. Examples that can be cited are the Michelson (FIG. 2A) and Mirau (FIG. 2B) microscopes comprising a single objective LO with a reference mirror MR and a beam splitter secured to said objective and aligned along its optical axis. These setups are simpler and more compact than that of Linnik, but the introduction of an adjustable dispersion compensation device, as well as the possible displacement of element(s) of the interferometer, are more difficult. Examples of embodiments based on the Michelson and Mirau configurations using an immersion medium IM to compensate the dispersion difference between the two arms of the interferometer without the need for moving parts inside the interferometer are illustrated in FIGS. 5A (Michelson configuration with objective in air), 5B (Michelson configuration with immersion objective), 5C (Michelson configuration with observation window HO and objective in air—note that the window can be replaced by a hole and/or the objective can be an immersion objective; if the window is present, a transparent plate of the same thickness must be provided in the reference arm), 5D (Mirau configuration with objective in air), 5E (Mirau configuration with immersion objective and window), 5F (Mirau configuration with objective in air and window) and 5G (Mirau configuration with immersion objective, without window).

Figure 5C:
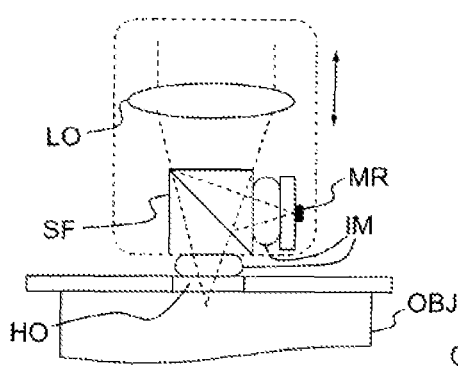
Figure 5D:
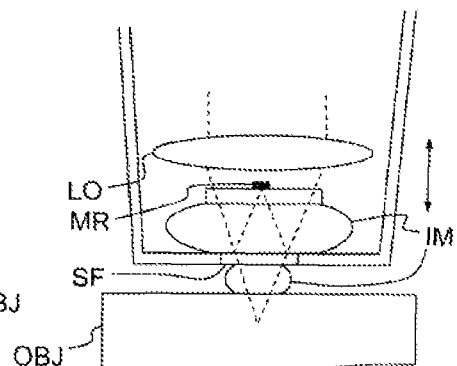
Figure 5E:
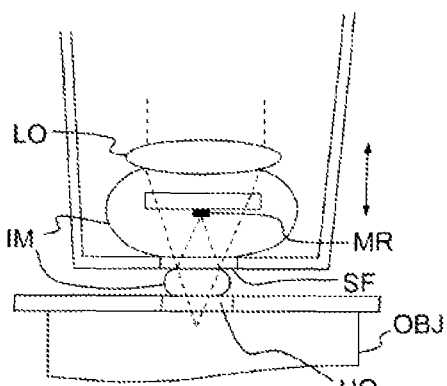
Figure 5F:
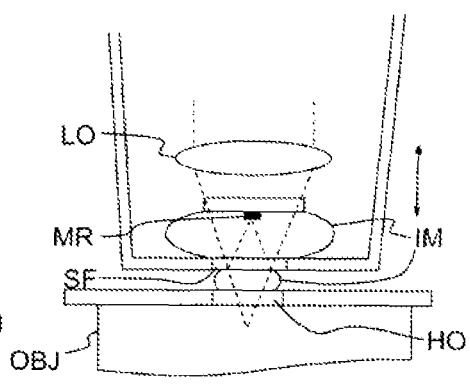
Figure 5G:
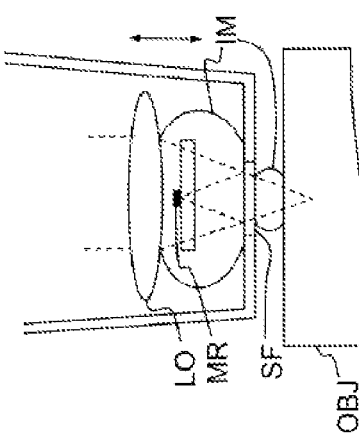

In the devices of FIGS. 5D to 5G, the reference mirror is formed by a transparent plate that has a small reflective zone at its center, produced for example by a metal or dielectric deposition or induced by the refractive index of the plate itself. In the embodiments of FIGS. 5C, 5D and 5G, the reflective zone is formed on the rear face of the transparent plate, which serves to compensate the dispersion introduced, in the object arm, by the window (FIG. 5C) or the beam splitter (5D, 5G). Otherwise, it is formed on the front face of the plate. Furthermore, in the embodiments of FIGS. 5D to 5G, the beam splitter consists of a plate that has a suitable coefficient of reflection (typically between 10% and 50%) on one of its faces; the splitting is done on the front face of this plate in the case of FIGS. 5D and 5G, and on the rear face in the case of FIGS. 5E and 5F. The "front" and "rear" faces are defined in relation to the direction of propagation of the light beam incident on the plate.

Figure 6:
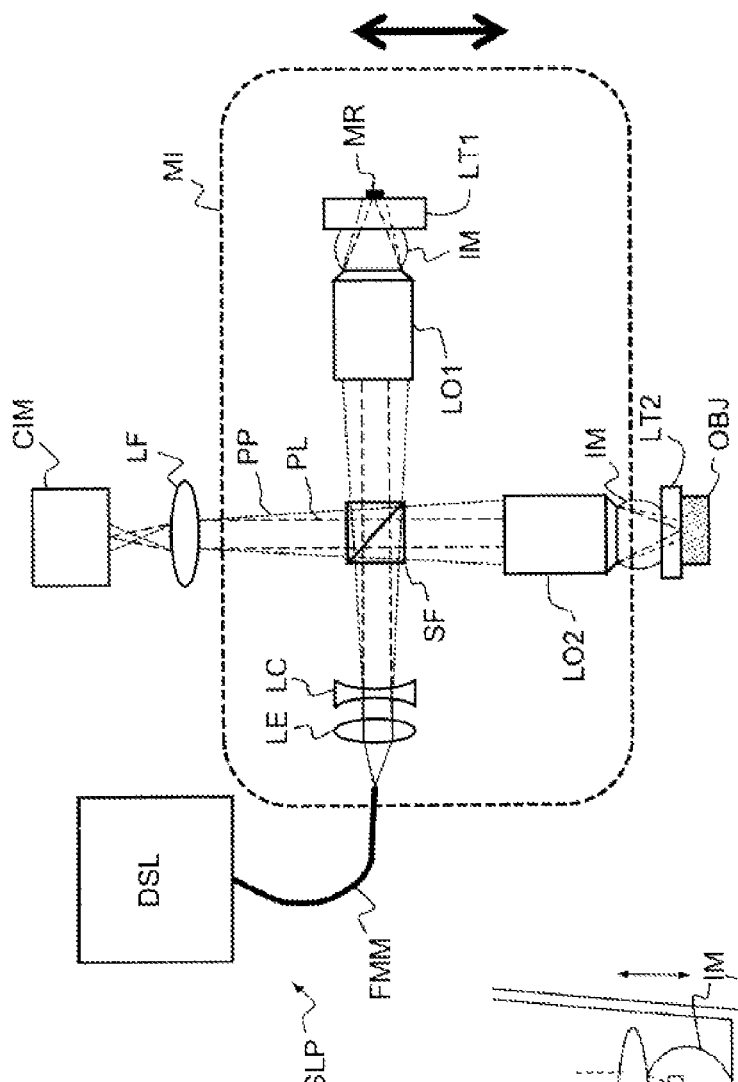
FIG. 6, another embodiment of the invention based on a Linnik interferometric microscope and using an immersion medium.

FIG. 6 illustrates another embodiment of the invention in which:

The interferential microscope MI is of the Linnik type.

The objectives LO1, LO2 are of the immersion type. Thus, the dispersion compensation is produced by two drops of an immersion medium IM. Each of these drops is gripped between an objective (LO1, LO2) and a transparent plate (LT1, LT2). The reference mirror is produced by the rear face (opposite the objective LO1) of the plate LT1 (face possibly treated to adjust its coefficient of reflection), while the object OBJ is pressed against the rear face of the plate LT2.

The polychromatic light source SLP is spatially coherent. It comprises a primary polychromatic source, which is in particular a superluminescent diode DSL exhibiting a temporal coherence length of the order of 1 to 20 µm, and a single-mode optical fiber FMM (optional). The light generated by the superluminescent diode is injected into a so-called input end of the fiber FMM, exits from the opposite (output) end of said fiber and is collimated by a lens LE.

The spatial coherence of the illumination makes it possible to produce a particularly simple confocal filtering that does not require any slit and that comprises just one cylindrical lens LC divergent on the side of the light source (in fact, of the output end of the optical fiber) and a spherical lens LF arranged in front of the sensor CIM, of one-dimensional type. The cylindrical lens LC creates an astigmatism by making the light beam divergent in the plane of the figure but not in a perpendicular plane (the dotted line PP represents a section of the light beams in the plane of the figure, whereas the dashed line PL represents a section of the light beams in a plane at right angles to the figure). The result thereof is an illumination of the object and of the reference mirror in the form of a line oriented according to the plane of the figure; the lens LF creates an image of this line on the one-dimensional optical sensor; the light not originating from the observation line reaches the single line of pixels of the sensor with an attenuated intensity, thus producing a one-dimensional confocal filtering. As a variant, it would be possible to use a convergent cylindrical lens to also make the system astigmatic.

The axial scan is performed by displacing the interferometric microscope as a whole—including the output end of the fiber FMM and the astigmatic optical system formed by the lenses LE and LC—relative to the object OBJ and to the transparent plate LT2. The optical sensor CIM and the associated lens LF can equally be displaced with the interferometric microscope or not (the second option is illustrated in the figure); it is however necessary for the sensor CIM to remain in the focal plane (or more generally the focusing plane) of the lens LF.

Figure 3A:
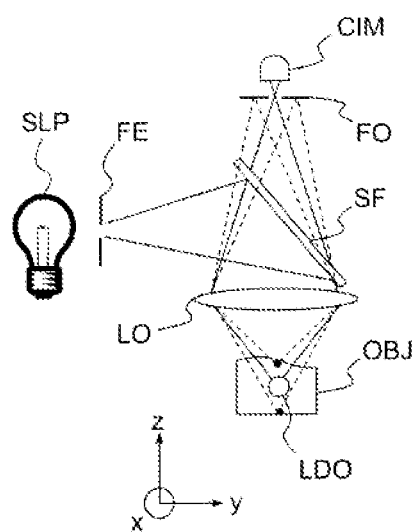
FIGS. 3A and 3B, the principle of slit confocal filtering.
Figure 3B:
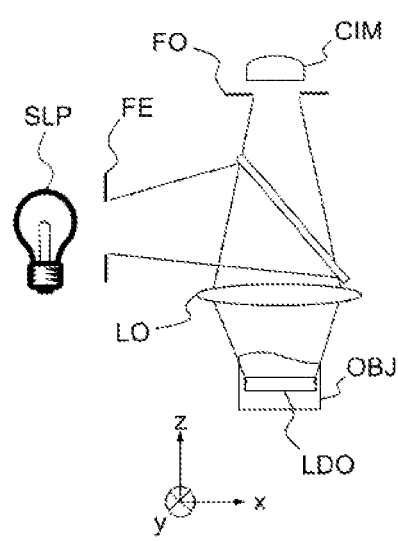
Figure 4A:
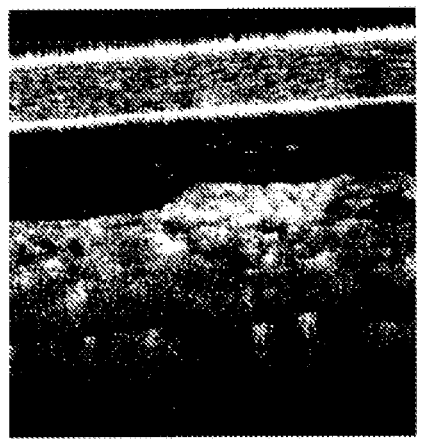
FIGS. 4A and 4B, respectively, an image obtained by using an optical coherence tomography apparatus according to the prior art and an image of the same object obtained by using an optical tomography apparatus according to the invention.
Figure 4B:

FIGS. 3A and 3B review the principle of operation of a slit confocal microscope. In a plane at right angles to the spatial filtering slit FO (plane zy in FIG. 3A), the slit FO allows the light originating from the region of the object where the slit FE is focused by the objective LO (beam represented by unbroken line) to pass, and attenuates the light originating from other regions of the object (dotted line beams for example). In a plane parallel to the slit (plane zx in FIG. 3A), such a filtering does not occur. The result is that an "observation line" LDO is defined in the focusing plane of the objective and oriented like the slits FE and FO. The focusing planes are the planes at right angles to the optical axis, where the images of the input slit FE, if present, are formed. More generally, the focusing plane of the object arm is that where the observation line LDO is formed; its conjugate plane is the focusing plane in the observation arm; and the focusing plane of the reference arm is that where an illumination line is formed in this arm. If the input light beam is collimated in the plane orthogonal to the observation or illumination line, as in FIGS. 1A, 1B, the focusing planes correspond with the focal planes of the objective or objectives.

An apparatus according to the invention thus comprises two means that make it possible to select the light originating from a determined region of the object: the confocal filtering and the "coherence gate" defined by "white" light interferometry. These means are complementary: the confocal filtering enhances the performance levels of the interferometric imaging by reducing the "background" produced by the scattering of the light and by stray reflections. A greater part of the dynamic range of the sensor is thus used to detect the useful interferometric signal.

In effect, biological tissues scatter strongly; the number of ballistic photons (not having undergone scattering other than a single backscattering) decreases exponentially with depth. Now, interferometry—even with low coherence length—does not make it possible to distinguish between a ballistic photon originating from the region imaged in the object and a photon originating from other regions of the object and having covered an optical trajectory of the same length because of the scatterings undergone. The result there is a spurious interferometric signal which is added to the useful interferometric signal, creating artifacts in the images and limiting the accessible imaging depth. In the device of the invention, the confocal filtering removes a large amount of the photons other than the ballistic photons originating from the zone imaged, eliminating this background; indeed, the slit confocal filtering is not perfect because it acts only in one dimension, but the reduction of this "background noise" remains significant.

Compared to confocal filtering alone, the use of an interferometric detection allows for a considerable amplification of the useful signal (in the case of the "pure" confocal microscopy, it is the low signal-to-noise ratio which limits the acquisition depth). In the apparatus of the invention there is therefore synergy—and not simple juxtaposition—between the two principles involved: microscopy by interferometry with low coherence length and slit confocal microscopy.

The use of confocal filtering through a hole, instead of a slit confocal filtering, would considerably slow down the acquisition of the images (an additional scan would be necessary) without providing any significant advantage in terms of accessible imaging resolution and/or depth.

The device can still exhibit acceptable performance levels even if the confocal filtering is not effective. This situation occurs when objectives of relatively large depth of field (typically greater than or equal to 10 µm), and/or quite wide input and output slits and/or a one-dimensional detector having large-sized pixels (rectangular for example) or having several rows of pixels are used. In this case, it is the interferometric detection with low temporal coherence which determines the performance levels in terms of axial resolution and accessible imaging depth. But the benefit of illuminating along a line and the detection of this line using a one-dimensional sensor is still present, because that still makes it possible to produce images in vertical section at high speed.

The technique of the invention is much better suited than full-field OCT to in vivo applications. In these applications, the "object" is a living organism (a patient for example) which is likely to move during the acquisition of the interferometric signal, scrambling the latter. According to the invention, an interferometric signal is acquired for each line, in a very short time, for example of the order of $10^{-4}$ second, which makes it possible to overcome the problems of movement of the object. By contrast, in full-field OCT, the interferometric signal is acquired by a combination of a plurality of two-dimensional images acquired by a matrix camera, which takes much longer.

Compared to the abovementioned technique of Yu Chen et al., the invention offers the advantage of directly providing images of vertical slices of the object observed, often more useful than "face wise" images.

A prototype of the invention has been produced, using halogen lamp illumination, of objectives with a numerical aperture of 0.15 in air and a Linnik configuration. This prototype was tested by using as observed object a display card for an infrared beam with a thickness of approximately 500 µm, comprising two plastic layers enclosing a granular plastic containing microstructures, a non-scattering region and a layer of fluorophores. The same object was imaged by using a scanning OCT apparatus on the market (ThorLabs). FIG. 5A shows the image (vertical slice) obtained with the apparatus on the market, FIG. 5B that obtained with the prototype of the invention. The point at which the resolution is better in the case of the invention can be noted.

It is interesting to note that, with appropriate dimensioning, an apparatus according to the invention can exhibit an essentially "isotropic" spatial resolution, of the order of 1 µm, both axially and laterally.

The invention claimed is:

1. An optical tomography apparatus comprising:
   a polychromatic light source;
   a one-dimensional optical sensor;
   an interferometric microscope comprising: a reference arm, at the end of which is arranged a reference mirror; an object arm; a beam splitter coupling said reference arm and said object arm to said polychromatic light source and to said sensor, and a first objective situated in the reference arm, said reference mirror being arranged in a focusing plane, situated in the reference arm, of said first objective,
   a one-dimensional confocal spatial filter, cooperating with said polychromatic light source to illuminate an object to be observed, arranged in said object arm, with an observation line,
   wherein said observation line comprises a line of light that lies in a focusing plane of a second objective, situated in the object arm, and extends perpendicular to an optical axis of said second objective,
   wherein a one-dimensional image of said observation line is formed on said sensor,
   wherein the apparatus further comprises:
   at least one actuator configured to displace said observation line in a depth wise direction and parallel to the optical axis of said second objective, extending along the object arm, so as to perform a depth scan of said object, while maintaining a zero optical path difference between, on the one hand, a first trajectory going from said beam splitter to said reference mirror and back by traveling along said reference arm and, on the other hand, a second trajectory going from said beam splitter to said observation line and back by traveling along said object arm; and
   a processor programmed or configured to reconstruct a two-dimensional image of a section of said object to be observed, oriented parallel to said optical axis of said second objective, extending along the object arm, from a plurality of one-dimensional interferometric images acquired by said sensor corresponding to different positions of said observation line during said depth scan.

2. The apparatus of claim 1, wherein said one-dimensional confocal spatial filter is also arranged to select the light backscattered by said object and originating from said observation line.

3. The apparatus of claim 1, wherein said at least one actuator is configured to provoke a relative displacement, parallel to said optical axis of said second objective placed in the object arm, of said object to be observed relative to said interferometric microscope, without modifying the optical lengths of said reference arm and of said object arm.

4. The apparatus of claim 1, wherein said at least one actuator is configured to displace the second objective in the focusing plane of which said observation line is located and to modify the optical length of said reference arm so as to maintain the zero optical path difference between said first trajectory and said second trajectory.

5. The apparatus of claim 1, also comprising a dispersion compensator arranged on at least one out of said object arm and said reference arm, said at least one actuator being configured to act also on said dispersion compensation device during said depth scan.

6. The apparatus of claim 1, wherein said interferometric microscope is a Linnik interferometric microscope, said first objective is arranged on said reference arm and said second objective is arranged on said object arm, said reference and object arms being separate.

7. The apparatus of claim 6, wherein said first and second objectives are immersion objectives, and in which said at least one actuator is configured to provoke a relative displacement, parallel to said optical axis of said second objective placed in the object arm, of said object to be observed relative to said interferometric microscope, without modifying the optical lengths of said reference arm and of said object arm.

8. The apparatus of claim 1, wherein said polychromatic light source is spatially coherent and said confocal filter comprises an astigmatic optical system arranged between said polychromatic light source and the beam splitter, a lens arranged in front of said one-dimensional optical sensor and the one-dimensional optical sensor itself arranged in a focusing plane of said lens.

9. An optical tomography method comprising the following steps:
   a) providing a polychromatic light source;
   b) using a beam splitter to direct a first fraction of light emitted by said source along a first trajectory, called reference trajectory, and a second fraction of light emitted by said source along a second trajectory, called object trajectory;
   c) using an objective cooperating with a one-dimensional confocal spatial filter to focus said second fraction of light so as to illuminate a semi-transparent object to be observed with an observation line, wherein said observation line comprises a line of light that lies in a focusing plane of said objective, situated in an object arm, and extends perpendicular to said optical axis of said objective, and to collect the light backscattered by said illuminated object;
   d) using said objective, or another objective, to focus said first fraction of light on a reference mirror arranged on said reference trajectory, and to collect the light reflected by said reference mirror;
   e) using said beam splitter to combine the light backscattered by said object with the light reflected by said reference mirror and direct it to a one-dimensional optical sensor;
   f) forming a one-dimensional image of said observation line on said sensor;
   g) using at least one actuator to displace said observation line in a depth wise direction and parallel to an optical axis of said objective so as to perform a depth scan of said object to be observed on said object trajectory, while maintaining a zero optical path difference between said reference trajectory and said object trajectory; and
   h) using a processor to reconstruct a two-dimensional image of a section of said object to be observed, oriented parallel to said optical axis, from a plurality of one-dimensional interferometric images acquired by said sensor corresponding to different positions of said observation line during said depth scan.

10. The method of claim 9, wherein step f) also comprises selecting the light originating from said observation line.

11. The method of claim 9, wherein said step g) is implemented by provoking a relative displacement, parallel to said optical axis, of said object to be observed relative to said interferometric microscope without modifying the optical lengths of said reference trajectory and of said object trajectory.

12. The method of claim 9, wherein said step g) is implemented by displacing the objective in a focusing plane of which said observation line is located and by modifying the optical length of said reference trajectory so as to maintain the zero optical path difference between said first trajectory and said second trajectory.

13. The method of claim 9, also comprising a step i) of compensation of the modifications of the dispersion induced by the displacement of the observation line inside said object to be observed during said depth scan.

14. The method of claim 9, wherein said object to be observed is a biological tissue.

15. An optical tomography apparatus comprising:
   a polychromatic light source;
   a one-dimensional optical sensor;
   an interferometric microscope comprising: a reference arm, at the end of which is arranged a reference mirror; an object arm; a beam splitter coupling said reference arm and said object arm to said polychromatic light source and to said sensor, and a single objective, said reference mirror being arranged in a first focusing plane, situated in the reference arm, of said objective;
   a one-dimensional confocal spatial filter, cooperating with said polychromatic light source to illuminate an object to be observed, arranged in said object arm, with an observation line;
   at least one actuator configured to displace said observation line in a depth wise direction and parallel to the optical axis of said objective, extending along the object arm, so as to perform a depth scan of said object, while maintaining a zero optical path difference between, on the one hand, a first trajectory going from said beam splitter to said reference mirror and back by traveling along said reference arm and, on the other hand, a second trajectory going from said beam splitter to said observation line and back by traveling along said object arm; and a processor programmed or configured to reconstruct a two-dimensional image of a section of said object to be observed, oriented parallel to said optical axis of said objective, extending along the object arm, from a plurality of one-dimensional interferometric images acquired by said sensor corresponding to different positions of said observation line during said depth scan, wherein said observation line comprises a line of light that lies in a second focusing plane, situated in the object arm, of said objective and extends perpendicular to an optical axis of said objective, wherein a one-dimensional image of said observation line is formed on said sensor, and wherein said interferometric microscope is chosen from a Michelson interferometric microscope and a Mirau interferometric microscope.

16. The apparatus of claim 15, wherein said interferometric microscope is a Mirau interferometric microscope comprising the single objective, and the reference mirror and the beam splitter are secured to said single objective and aligned along its optical axis, said at least one actuator is configured to provoke a relative displacement, parallel to said optical axis, of said interferometric microscope relative to the object to be observed, an immersion medium is arranged, on the one hand, between said beam splitter and the object to be observed and, on the other hand, between said beam splitter and the reference mirror.

* * * * *